(12) United States Patent
Kim (10) Patent No.: US 11,241,540 B2
(45) Date of Patent: Feb. 8, 2022

(54) MANUAL INJECTOR FOR SKIN

(71) Applicant: HUMAN & BIZ. CO., LTD., Goyang-si (KR)

(72) Inventor: Mi Young Kim, Incheon (KR)

(73) Assignee: HUMAN & BIZ. CO., LTD., Gyeonggi-do (KR)

( * ) Notice: Subject to any disclaimer, the term of this patent is extended or adjusted under 35 U.S.C. 154(b) by 216 days.

(21) Appl. No.: 16/463,223

(22) PCT Filed: Oct. 16, 2017

(86) PCT No.: PCT/KR2017/011363
§ 371 (c)(1),
(2) Date: May 22, 2019

(87) PCT Pub. No.: WO2018/101599
PCT Pub. Date: Jun. 7, 2018

(65) Prior Publication Data
US 2020/0061293 A1   Feb. 27, 2020

(30) Foreign Application Priority Data
Dec. 2, 2016 (KR) .................. 10-2016-0163400

(51) Int. Cl.
*A61M 5/20* (2006.01)
*A61M 5/315* (2006.01)
*A61M 5/31* (2006.01)

(52) U.S. Cl.
CPC ...... *A61M 5/2033* (2013.01); *A61M 5/31511* (2013.01); *A61M 2005/2026* (2013.01); *A61M 2005/3128* (2013.01)

(58) Field of Classification Search
CPC ............ A61M 5/2033; A61M 5/31511; A61M 2005/2026; A61M 2005/3128;
(Continued)

(56) References Cited

U.S. PATENT DOCUMENTS

2008/0255520 A1* 10/2008 Henderson .............. A61M 5/19
604/191
2009/0028824 A1* 1/2009 Chiang ................... A61P 43/00
424/85.7
(Continued)

FOREIGN PATENT DOCUMENTS

KR   2003953590000    9/2005
KR   1020080100569    11/2008

*Primary Examiner* — Brandy S Lee
*Assistant Examiner* — Nidah M Hussain
(74) *Attorney, Agent, or Firm* — IPLA P.A.

(57) ABSTRACT

A manual injector for skin more easily percutaneously injects into the body liquid nutritional components having skin moisturization, anti-inflammation, skin irritation alleviation, whitening, and anti-wrinkle effects; and a therapeutic agent or an immune activation agent, such as a vaccine, or a skin elasticity nutritional component for skin care. The injector includes: a housing in which liquid nutritional components are charged; a coupling casing mounted to the housing; an opening and closing valve coupled to an inlet hole by passing therethrough and configured to be moveable upward and downward; a bottom casing; a pumping unit having a pressing bar provided therein; a top casing in which a needle hole is formed; and a needle.

3 Claims, 12 Drawing Sheets

(58) Field of Classification Search
CPC .............. A61M 5/3295; A61M 5/3298; A61M 37/0015; A61M 2037/0023; A61M 39/24; A61M 2039/242; A61M 2039/2473
USPC ........................................................ 604/214
See application file for complete search history.

(56) References Cited

U.S. PATENT DOCUMENTS

| | | | | |
|---|---|---|---|---|
| 2009/0099521 | A1* | 4/2009 | Gravesen | A61M 25/0606 604/136 |
| 2012/0275955 | A1* | 11/2012 | Haghgooie | A61B 5/154 422/44 |
| 2018/0264204 | A1* | 9/2018 | Mandaroux | A61M 5/3293 |

* cited by examiner

MANUAL INJECTOR FOR SKIN

BACKGROUND

The present invention relates to a manual injector for skin, the injector being capable of more easily percutaneously injecting into the body liquid nutritional components having skin moisturization, anti-inflammation, skin irritation alleviation, whitening, and anti-wrinkle effects; and a therapeutic agent or an immune activation agent, such as a vaccine, or a skin elasticity nutritional component for skin care.

The condition of the skin can greatly affect a person's appearance. Due to this, various methods are currently being used for the purpose of whitening, reducing wrinkles, moisturization, and elasticity enhancement of the skin in addition to treatment of skin disease.

Human skin is composed of three primary layers: the epidermis, the dermis, and the hypodermis. The dermis, which occupies the majority of the skin, is divided into two layers: the papillary layer and the reticular layer.

The papillary layer contains capillaries, lymph vessels, and the like. The reticular layer contains collagen that forms collagenous fibers related to formation of facial wrinkles, elastin that forms elastic fibers providing elasticity to the skin, ground substances, and the like.

The visual condition of the skin greatly depends on the condition of the dermis as described above. Therefore, various methods for improving the condition of the skin are mostly applied to the dermis.

Due to the fact that the dermis is protected by the epidermis, even when a drug to be delivered to the dermis is applied to the skin, the amount and speed of the drug reaching the dermis are highly likely to decrease.

In order to rapidly deliver a drug coated on the epidermis to the dermis, a method of applying pressure or ultrasonic vibration has been proposed.

Such a method has the advantage of causing no damage to the epidermis, but is problematic in that provision of a means for generating a desired pressure or ultrasonic vibration may lead to an increase in cost and volume.

In an effort to overcome such a problem, a method of forming a through hole in the epidermis with a microneedle (hereinafter referred to as a needle) and then applying a drug having a desired effect to the skin to deliver the drug to the dermis has been widely used.

As one example, Korean Patent No. 10-0921009 (hereinafter referred to as "related art 1"), entitled "Microneedle Roller Structure", is disclosed in which multiple needles are provided on the surface of a roller from which a drug flows out, whereby when the roller is rotated in contact with the skin, the needles puncture the skin to form multiple through holes in the epidermis, and at the same time the drug flowing out of the roller is easily delivered to the dermis.

However, the roller structure according to related art 1 is problematic in that due to the fact that the multiple needles are rotated in cooperation with rotation of the roller, linear long through holes extended in a tangential direction of the roller are formed in the skin rather than point-like through holes.

In other words, the roller structure according to related art 1 may cause more damage to the epidermis and the dermis than intended, and at the same time may cause more pain than necessary, and a recovery speed of the epidermis incised by the needles may be slower than the case where the point-like through holes are formed, leading to a high possibility of infection by germs or foreign substances introduced from outside.

In addition, when the drug that flows out of the roller and has a low viscosity is applied to the skin, there is a problem in that the drug may be highly likely to flow randomly along the skin.

As another example, Korean Utility Model Registration No. 20-0395359, entitled "Microneedle Roller" (hereinafter referred to as "related art 2"), is disclosed. The microneedle roller of related art 2 as disclosed in the publication (correction notice) includes a roller constituted by stacking at least one disc and at least one microneedle provided in the disc or on a surface of the disc. The microneedle is configured such that an end thereof has a predetermined length protruding from the outer surface of the roller, and the disc is provided with at least one hole formed radially from the center toward the outer peripheral surface of the disc such that the at least one microneedle is inserted into the hole.

Such a method of inducing collagen production and supplementation in the skin by stimulating the skin with sharp needles is based on the following theory.

That is, when the sharp needles press the skin, microchannels are formed in the skin tissue. The needles create micro-injuries in the skin tissue during such a procedure, and the micro-injuries stimulate skin's own natural healing process forming new skin tissue for more elastic skin and overall skin rejuvenation.

As the micro-injuries heal due to the natural healing process of the skin, new collagen that is essential for skin regeneration is naturally regenerated, resulting collagen production and replenishment for more elastic skin.

However, related art 2 is a roller type and thus is problematic in that scratches due to user's carelessness may occur during storage, and inserting of the needles is performed manually with much detail and attention, which may lead to inconvenience in manufacturing and inefficiency of time.

In addition, when a drug such as minoxidil, which has relatively strict restrictions on the application amount and the application area, is applied, there is a high possibility that the drug may be applied beyond a desired range.

Therefore, in order to directly deliver a drug to the dermis, it is necessary to propose a method that can allow the drug to be applied only within a desired range while minimizing damage to the epidermis.

SUMMARY OF THE INVENTION

Accordingly, the present invention has been made keeping in mind the above problems occurring in the related art, and an objective of the present invention is to provide a manual injector for skin, the injector being capable of easily applying, to the skin, liquid nutritional components that provide various nutrients to the skin for skin moisturization, anti-inflammation, skin irritation alleviation, whitening, and anti-wrinkle effects, while minimizing damage to the epidermis.

Another objective of the present invention is to provide a manual injector for skin, the injector being capable of stimulating the dermis between the epidermis and the hypodermis of the skin, thus activating skin tissue to maintain elastic skin and minimize skin aging.

Still another objective of the present invention is to provide a manual injector for skin, the injector being capable of conveniently mounted to a glass bottle for easy portability and being capable of efficiently injecting liquid nutritional components, which provide various nutrients to the skin for skin moisturization, anti-inflammation, skin irritation alleviation, whitening, and anti-wrinkle effects, into the skin through a needle by using a pumping function, thus being convenient, simple, and economically efficient while being used regardless of place.

In order to accomplish the above objectives, according to an aspect of the present invention, there is provided a manual injector for skin, the injector including: a housing in which liquid nutritional components that provide various nutrients to the skin for skin moisturization, anti-inflammation, skin irritation alleviation, whitening, and anti-wrinkle effects are charged; a coupling casing mounted on an outer periphery of an upper end opening of the housing and having an inlet hole formed in a center of the coupling casing, a coupling bracket integrally provided with an upper outer periphery of the inlet hole, and a containing chamber defined outside an outer periphery of the coupling bracket and in which the liquid nutritional components of the housing that provide various nutrients to the skin for skin moisturization, anti-inflammation, skin irritation alleviation, whitening, and anti-wrinkle effects are introduced and stored; an opening and closing valve coupled to the inlet hole by passing therethrough so as to be movable upward and downward; a bottom casing having a slide hole centrally provided in a first surface thereof at a position corresponding to an end of the opening and closing valve, peripheral through holes formed outside the slide hole in all directions at predetermined intervals, and a central through hole centrally provided in a second surface thereof in communication with the slide hole; a pumping unit coupled to the bottom casing so as to be slidable upward downward in the slide hole, and having a spring that is provided at a side of the pumping unit and has a first end fixed to the coupling bracket, a sliding bracket coupled to a second end of the spring, and a pressing bar provided in the through hole; a top casing having needle holes communicating with the through holes at positions above the through hole of the bottom casing; and a needle coupled in the bottom casing and sequentially passing through each of the through holes and each of the needle holes, and having a discharge hole centrally formed therein.

The opening and closing valve may include:

an opening and closing member provided at a first side of the valve and coupled to the inlet hole by passing therethrough, the opening and closing member being configured to be movable upward and downward in the inlet hole so as to open and close the upper end opening of the housing, and having a smaller diameter than the inlet hole such that an inlet through hole is defined between an outer periphery of the opening and closing member and an inner wall of the inlet hole; and a plate body provided at a second side of the valve and having a larger diameter than the inlet hole so as to be seated over the inlet hole, the plate body having multiple holes formed therein such that the liquid nutritional components that provide various nutrients to the skin for skin moisturization, anti-inflammation, skin irritation alleviation, whitening, and anti-wrinkle effects are introduced therethrough.

According to another aspect of the present invention, there is provided a manual injector for skin, the injector including: a housing in which liquid nutritional components that provide various nutrients to the skin for skin moisturization, anti-inflammation, skin irritation alleviation, whitening, and anti-wrinkle effects are charged; a main body including a fastening cylinder provided at a first end of the main body so as to be mounted on an outer periphery of an upper end opening of the housing and having an inlet hole formed in a center of the fastening cylinder, an inner cylinder having a hollow cylindrical shape and provided in the fastening cylinder such that a first end thereof is seated on an inner surface of the fastening cylinder, a sliding cylinder provided at a second end of the inner cylinder and having a fastening protrusion centrally provided at a surface of the sliding cylinder and multiple needle insertion holes circumferentially formed outside an outer periphery of the fastening protrusion, and an opening and closing plate body coupled to the fastening protrusion and having a first side portion provided with an insertion hole centrally formed therein, and having a funnel shaped second side portion; a top casing provided at a second end of the main body and having needle holes communicating with the needle insertion holes; and a needle coupled in the main body and sequentially passing through each of the needle insertion holes and each of the needle holes, and having a discharge hole centrally formed therein.

The present invention can easily apply, to the skin, liquid nutritional components that provide various nutrients to the skin for skin moisturization, anti-inflammation, skin irritation alleviation, whitening, and anti-wrinkle effects, while minimizing damage to the epidermis. In addition, the present invention can stimulate the dermis between the epidermis and the hypodermis of the skin, thus activating skin tissue to maintain elastic skin and minimize skin aging. In particular, the present invention can be conveniently mounted to a glass bottle for easy portability and can efficiently inject the liquid nutritional components, which provide various nutrients to the skin for skin moisturization, anti-inflammation, skin irritation alleviation, whitening, and anti-wrinkle effects, into the skin through a needle by using a pumping function. Therefore, the present invention can be convenient, simple, and economically efficient while being used regardless of place.

DETAILED DESCRIPTION OF THE INVENTION

A manual injector for skin is provided. The injector includes: a housing 10 in which liquid nutritional components that provide various nutrients to the skin for skin moisturization, anti-inflammation, skin irritation alleviation, whitening, and anti-wrinkle effects are charged;

a coupling casing 20 mounted on the outer periphery of an upper end opening of the housing 10 and having an inlet hole 200 formed in the center of the coupling casing, a coupling bracket 210 integrally provided with the upper outer periphery of the inlet hole 200, and a containing chamber 220 defined outside the outer periphery of the coupling bracket 210 and in which the liquid nutritional components of the housing 10 that provide various nutrients to the skin for skin moisturization, anti-inflammation, skin irritation alleviation, whitening, and anti-wrinkle effects are introduced and stored;

an opening and closing valve 30 coupled to the inlet hole 200 by passing therethrough so as to be movable upward and downward;

a bottom casing 40 having a slide hole 410 centrally provided in a first surface thereof at a position corresponding to an end of the opening and closing valve 30, peripheral through holes 420 formed outside the slide hole 410 in all directions at predetermined intervals, and a central through hole 430 centrally provided in a second surface thereof in communication with the slide hole 410;

a pumping unit 50 coupled to the bottom casing 40 so as to be slidable upward downward in the slide hole 410, and having a spring 500 that is provided at a side of the pumping unit and has a first end fixed to the coupling bracket 210, a sliding bracket 510 coupled to a second end of the spring 500, and a pressing bar 520 provided in the through hole 430;

a top casing 60 having needle holes 600 communicating with the through holes 420 at positions above the through hole 430 of the bottom casing 40; and a needle 70 coupled in the bottom casing and sequentially passing through each of the through holes 420 and each of the needle holes 600, and having a discharge hole 700 centrally formed therein.

In the following description, the structural or functional description specified to exemplary embodiments according to the concept of the present invention is intended to describe the exemplary embodiments, so it should be understood that the present invention may be variously embodied, without being limited to the exemplary embodiments. The exemplary embodiments according to the concept of the present invention may be variously modified and may have various shapes, so examples of which are illustrated in the accompanying drawings will be described in detail with reference to the accompanying drawings. However, it should be understood that the exemplary embodiments according to the concept of the present invention are not limited to the embodiments which will be described hereinbelow with reference to the accompanying drawings, but various modifications, equivalents, additions and substitutions are possible, without departing from the scope and spirit of the invention. All terms or words used in the specification and claims have the same meaning as commonly understood by one of ordinary skill in the art to which inventive concepts belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. Specific structural and functional descriptions of embodiments of the present invention disclosed herein are only for illustrative purposes of the preferred embodiments of the present invention, and the present description is not intended to represent all of the technical spirit of the present invention. On the contrary, the present invention is intended to cover not only the exemplary embodiments, but also various alternatives, modifications, equivalents and other embodiments that may be included within the spirit and scope of the present invention as defined by the appended claims.

Unless otherwise defined, all terms including technical and scientific terms used herein have the same meaning as commonly understood by one of ordinary skill in the art to which the present invention belongs. It will be further understood that terms used herein should be interpreted as having a meaning that is consistent with their meaning in the context of this specification and the relevant art and will not be interpreted in an idealized or overly formal sense unless expressly so defined herein.

Hereinafter, a specific configuration and operation of a manual injector for skin according to the present invention will be described in detail with reference to the accompanying drawings.

Figure 1:
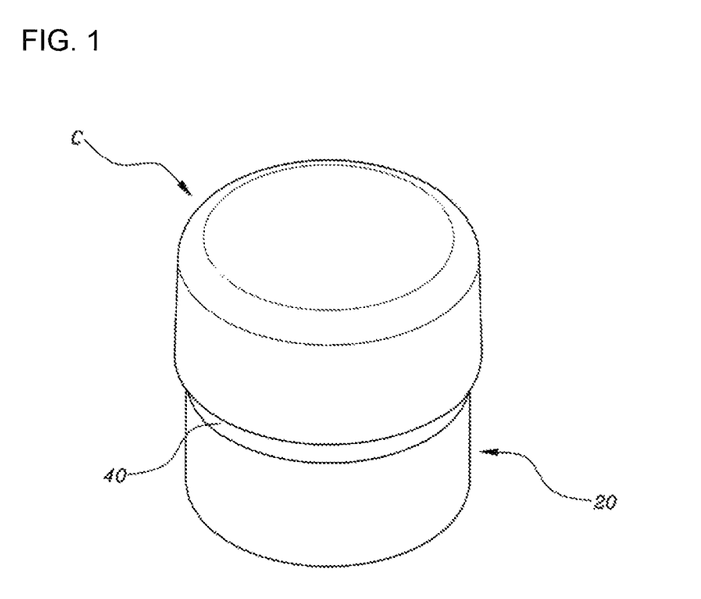
FIG. 1 is a perspective view showing a first embodiment of a manual injector for skin according to the present invention.
Figure 2:
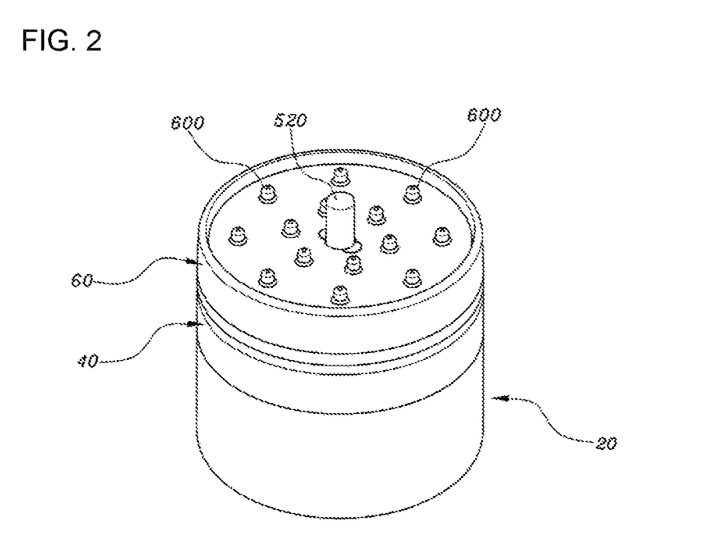
FIG. 2 is a perspective view showing a state in which a casing is removed in the first embodiment of the manual injector for skin according to the present invention of FIG. 1.
Figure 3:
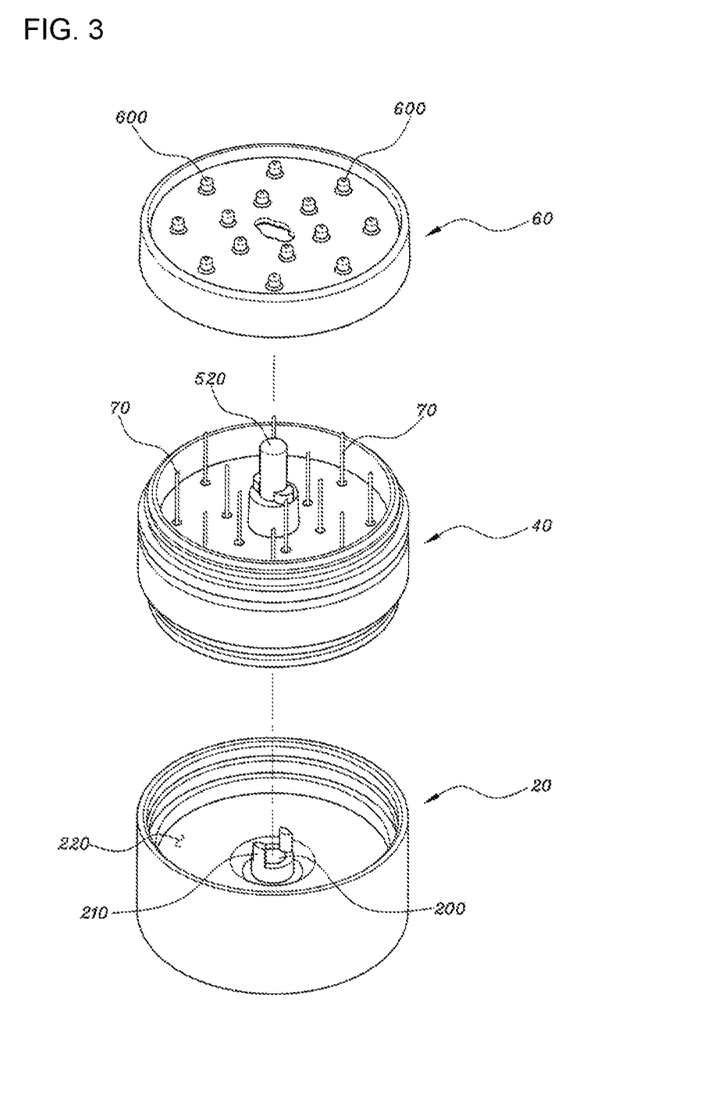
FIG. 3 is an exploded perspective view showing a state in which the casing is removed in the first embodiment of the manual injector for skin according to the present invention of FIG. 1.
Figure 4:
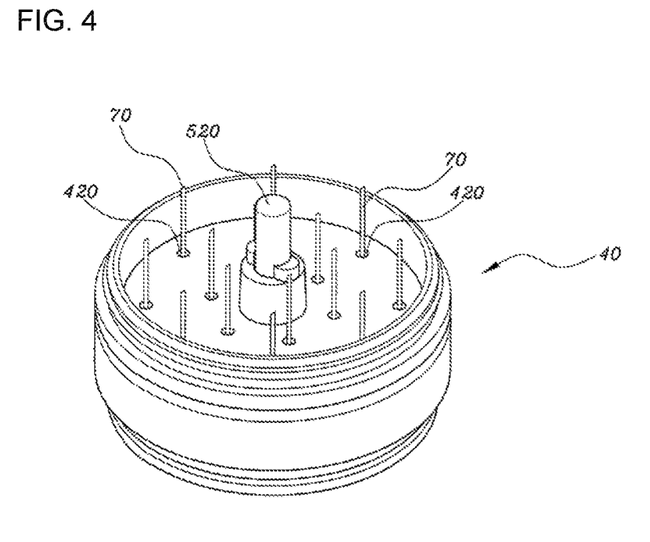
FIG. 4 is a perspective view showing a bottom casing in the first embodiment of the manual injector for skin according to the present invention of FIG. 1.
Figure 5:
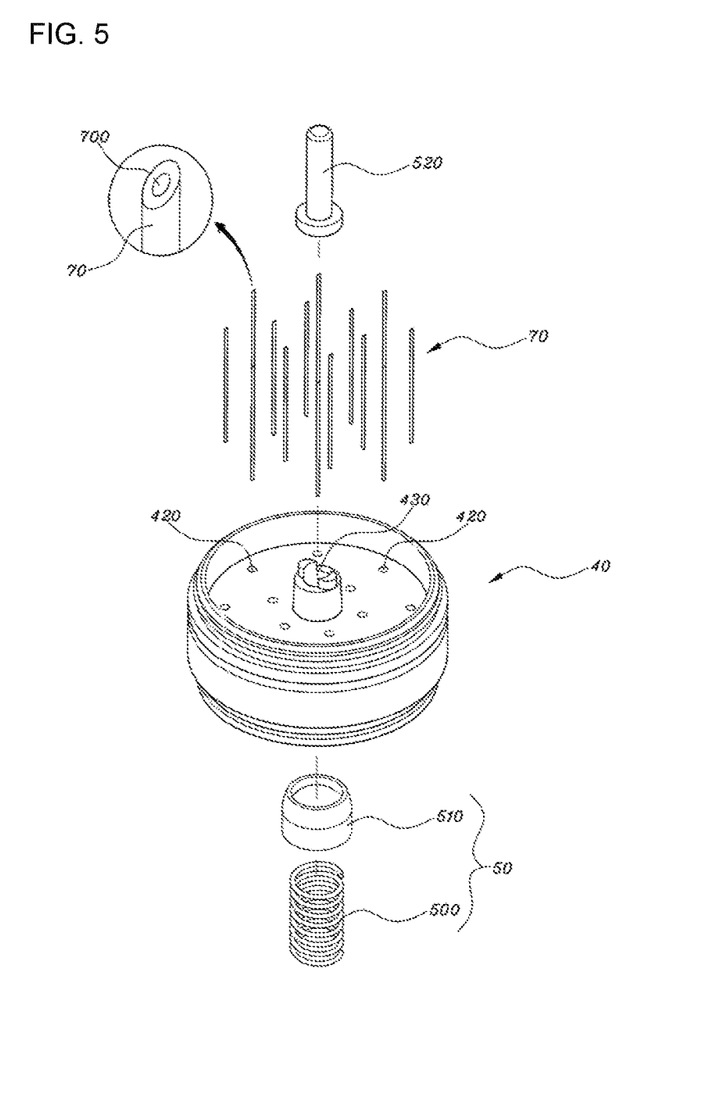
FIG. 5 is an exploded perspective view showing a state in which a pumping unit is separated from the bottom casing in the first embodiment of the manual injector for skin according to the present invention of FIG. 1.
Figure 6:
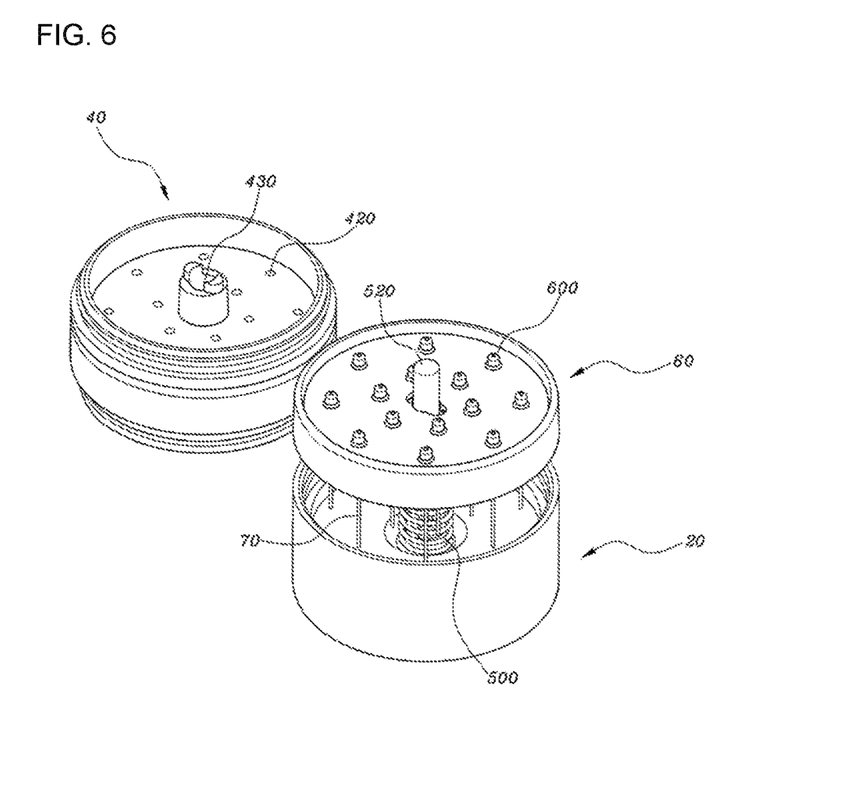
FIG. 6 is a perspective view a state in which the bottom casing is turned to one side with the casing removed in the first embodiment of the manual injector for skin according to the present invention of FIG. 1.
Figure 7:
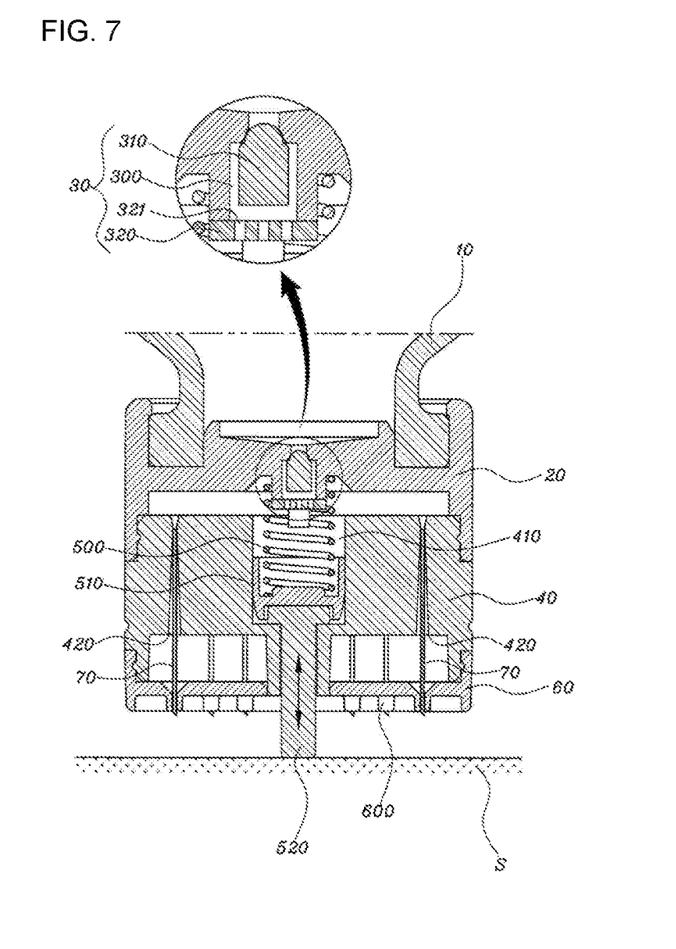
FIG. 7 is an internal sectional view showing a state in which a housing is coupled and the casing is removed in the first embodiment of the manual injector for skin according to the present invention of FIG. 1.
Figure 8:
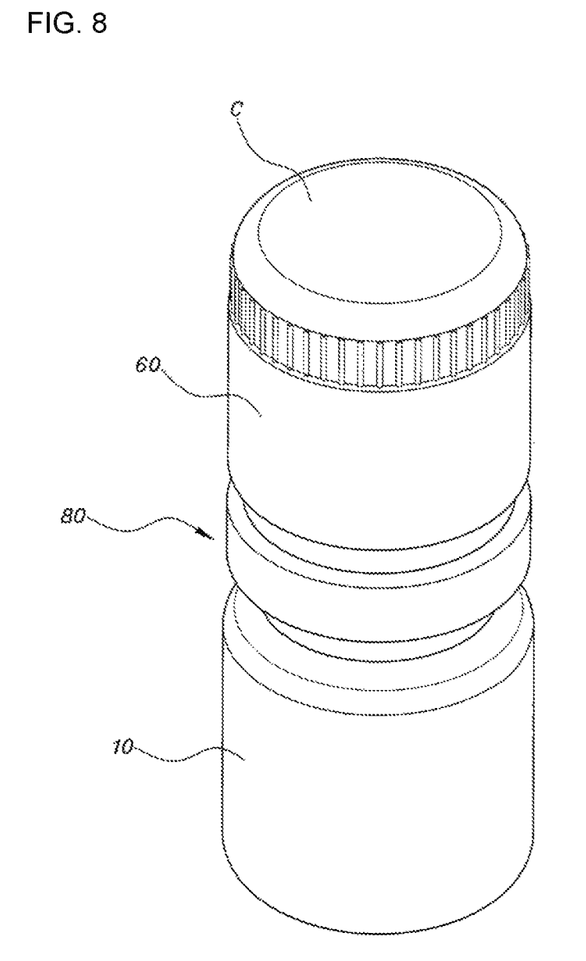
FIG. 8 is a perspective view a second embodiment of a manual injector for skin according to the present invention.
Figure 9:
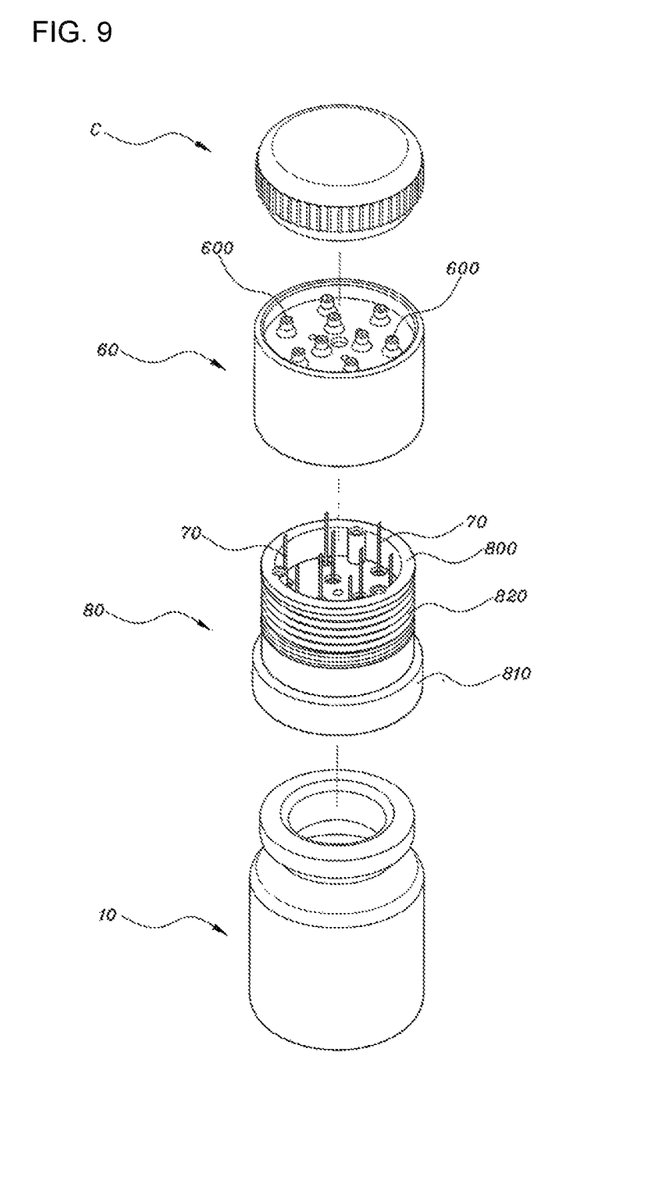
FIG. 9 is an exploded perspective view showing the second embodiment of the manual injector for skin according to the present invention of FIG. 8.
Figure 10:
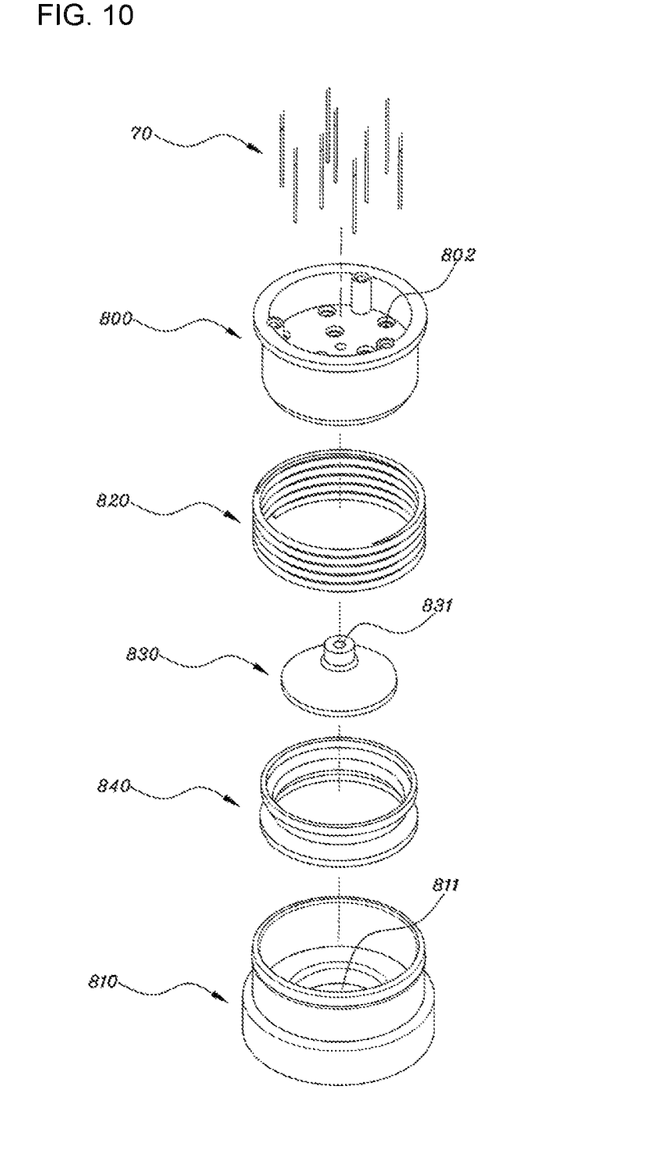
FIG. 10 is an exploded perspective view showing a main body in the second embodiment of the manual injector for skin according to the present invention of FIG. 8.
Figure 11:
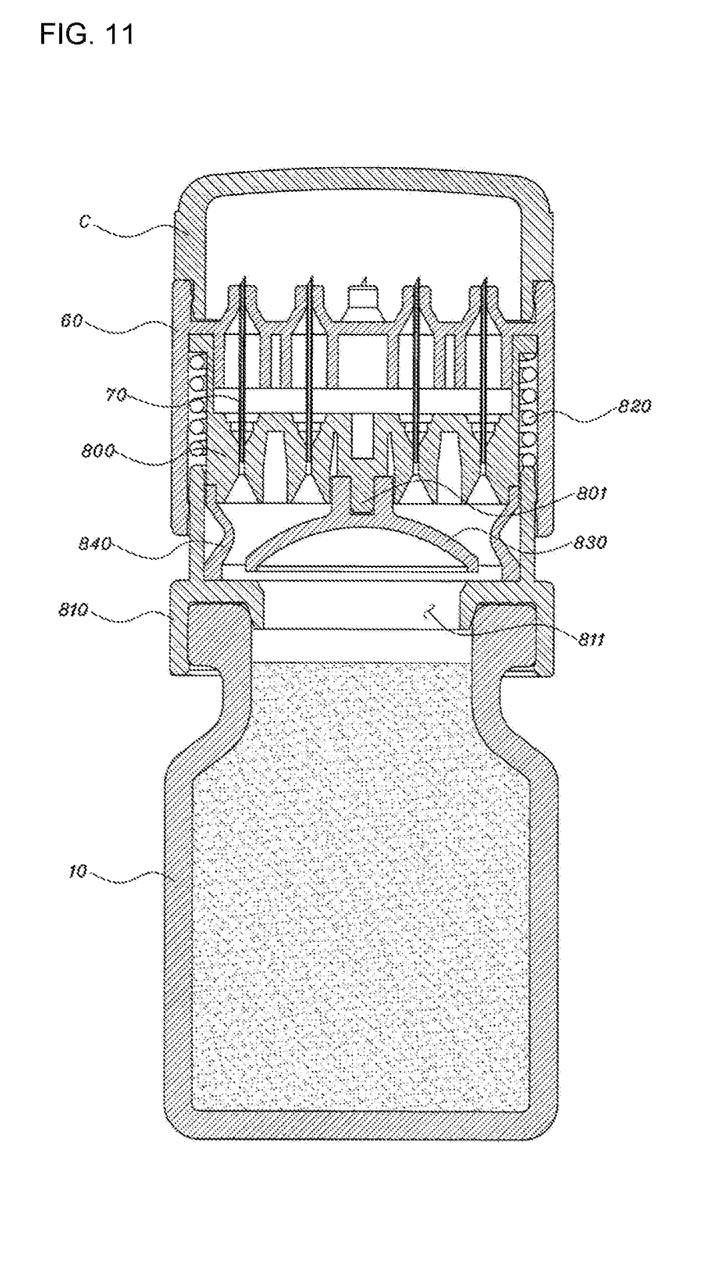
FIG. 11 is an assembled sectional view showing the second embodiment of the manual injector for skin according to the present invention of FIG. 8.
Figure 12:
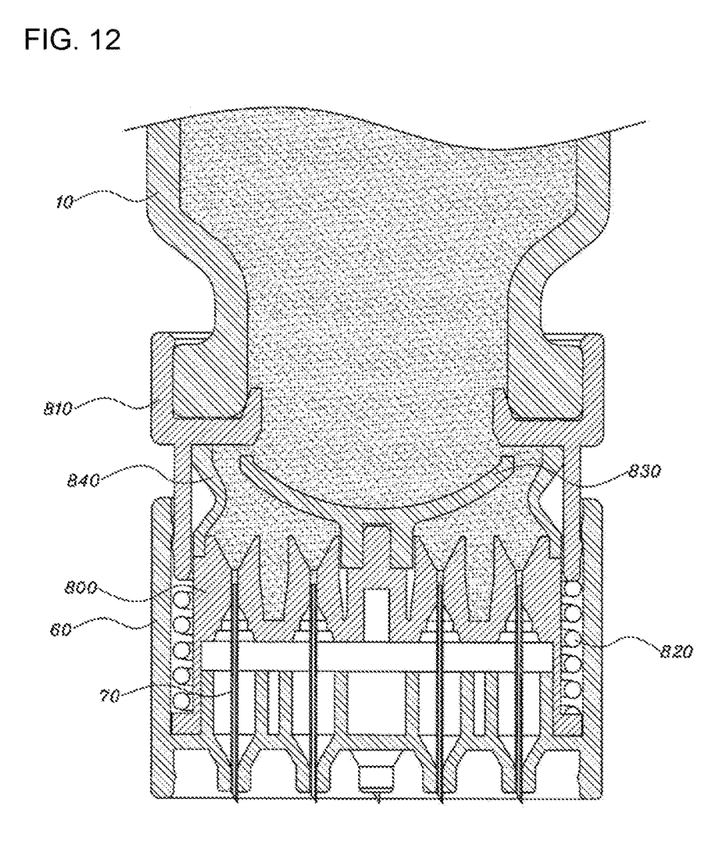
FIG. 12 is a sectional view showing a state before a housing is pressed after a casing is removed in the second embodiment of the manual injector for skin according to the present invention of FIG. 8.
Figure 13:
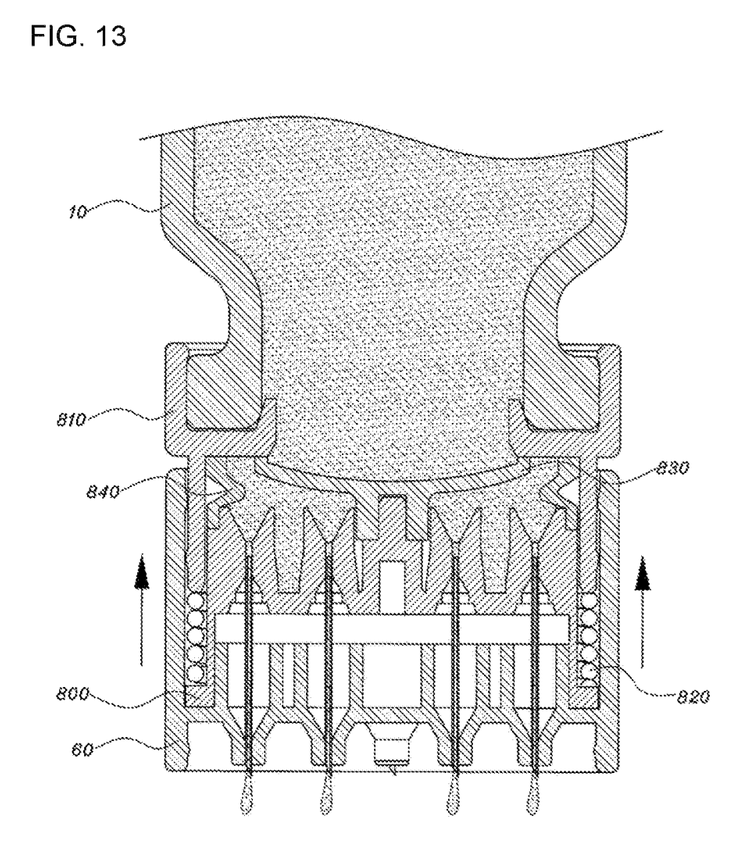
FIG. 13 is a sectional view showing a state in which the housing is pressed with the casing removed in the second embodiment of the manual injector for skin according to the present invention of FIG. 8.

FIG. 1 is a perspective view showing a first embodiment of a manual injector for skin according to the present invention, FIG. 2 is a perspective view showing a state in which a casing is removed in the first embodiment of the manual injector for skin according to the present invention of FIG. 1, FIG. 3 is an exploded perspective view showing a state in which the casing is removed in the first embodiment of the manual injector for skin according to the present invention of FIG. 1, FIG. 4 is a perspective view showing a bottom casing in the first embodiment of the manual injector for skin according to the present invention of FIG. 1, FIG. 5 is an exploded perspective view showing a state in which a pumping unit is separated from the bottom casing in the first embodiment of the manual injector for skin according to the present invention of FIG. 1, FIG. 6 is a perspective view a state in which the bottom casing is turned to one side with the casing removed in the first embodiment of the manual injector for skin according to the present invention of FIG. 1, FIG. 7 is an internal sectional view showing a state in which a housing is coupled and the casing is removed in the first embodiment of the manual injector for skin according to the present invention of FIG. 1, FIG. 8 is a perspective view a second embodiment of a manual injector for skin according to the present invention, FIG. 9 is an exploded perspective view showing the second embodiment of the manual injector for skin according to the present invention of FIG. 8, FIG. 10 is an exploded perspective view showing a main body in the second embodiment of the manual injector for skin according to the present invention of FIG. 8, FIG. 11 is an assembled sectional view showing the second embodiment of the manual injector for skin according to the present invention of FIG. 8, FIG. 12 is a sectional view showing a state before a housing is pressed after a casing is removed in the second embodiment of the manual injector for skin according to the present invention of FIG. 8, and FIG. 13 is a sectional view showing a state in which the housing is pressed with the casing removed in the second embodiment of the manual injector for skin according to the present invention of FIG. 8.

Embodiment 1

Reference numeral 10 denotes a housing. The housing 10 as partially shown in FIG. 7 has no structural characteristic and may be a relatively small glass bottle. The housing is a glass bottle type in which liquid nutritional components that provide various nutrients to the skin for skin moisturization, anti-inflammation, skin irritation alleviation, whitening, and anti-wrinkle effects are charged.

Reference numeral 20 denotes a coupling casing. The coupling casing 20 as shown in FIG. 3 is mounted on the outer periphery of an upper end opening of the housing 10 and has: an inlet hole 200 formed in the center of the coupling casing, a coupling bracket 210 integrally provided with the upper outer periphery of the inlet hole 200; and a containing chamber 220 provided outside the outer periphery of the coupling bracket 210 and in which the liquid nutritional components of the housing 10 that provide various nutrients to the skin for skin moisturization, anti-inflammation, skin irritation alleviation, whitening, and anti-wrinkle effects are introduced and stored.

Reference numeral 30 denotes an opening and closing valve. As shown in FIGS. 3 and 7, the opening and closing valve 30 includes: an opening and closing member 310 provided at a first side of the valve and coupled to the inlet hole 200 by passing therethrough so as to be movable upward and downward; and a plate body 320 provided at a second side of the valve. In detail, the opening and closing member is coupled to the inlet hole 200 by passing therethrough and is configured to be movable upward and downward in the inlet hole 200 so as to open and close the upper end opening of the housing 10. The opening and closing member has a smaller diameter than the inlet hole 200 such that an inlet through hole 300 is defined between the outer periphery of the opening and closing member and the inner wall of the inlet hole. The plate body has a larger diameter than the inlet hole 200 so as to be seated over the inlet hole 200. The plate body has multiple holes 321 formed therein such that the liquid nutritional components that provide various nutrients to the skin for skin moisturization, anti-inflammation, skin irritation alleviation, whitening, and anti-wrinkle effects are introduced therethrough.

Reference numeral 40 denotes a bottom casing. As shown in FIGS. 3, 4, and 5, the bottom casing 40 has: a slide hole 410 centrally provided in a first surface thereof at a position corresponding to an end of the opening and closing valve 30; peripheral through holes 420 formed outside the slide hole 410 in all directions at predetermined intervals; and a central through hole 430 centrally provided in a second surface thereof in communication with the slide hole 410.

Reference numeral 50 denotes a pumping unit. As shown in FIGS. 5 and 7, the pumping unit 50 is coupled so as to be slidable upward downward in the slide hole 410 and has: a spring 500 provided at a side of the pumping unit and having a first end fixed to the coupling bracket 210, a sliding bracket 510 coupled to a second end of the spring 500, and a pressing bar 520 provided in the through hole 430.

Reference numeral 60 denotes a top casing. As shown in FIGS. 3 and 7, the top casing 60 has needle holes 600 communicating with the through holes 420 at positions above the through hole 430 of the bottom casing 40.

Reference numeral 70 denotes a needle. As shown in FIG. 7 and other figures, the needle 70 is coupled in the bottom casing 40 and sequentially passes through each of the through holes 420 and each of the needle holes 600. The needle has a discharge hole 700 centrally formed therein.

Unexplained reference numeral C denotes a casing, and unexplained reference numeral S denotes the skin of a person being treated.

The operation of the present invention having the above configuration will be described with reference to the drawings.

As shown in FIG. 7, the coupling casing is coupled to the housing 10 in a state in which the housing 10 stores therein the liquid nutritional components that provide various nutrients to the skin for skin moisturization, anti-inflammation, skin irritation alleviation, whitening, and anti-wrinkle effects.

Then, an operator presses the pressing bar 520 against the skin of the person being treated while holding the housing 10. At this time, the pressing bar 520 or the needles 70 have to be in a state of not being externally exposed by a cover member (not shown) such as a sponge. In this state, when the operator repeatedly presses the pressing bar against the skin of the person being treated, the pressing bar 70 presses the sliding bracket 510 such that the sliding bracket slides upward and downward while compressing the spring 500. This causes the opening and closing member 310 to be repeatedly moved upward and downward, whereby the liquid nutritional components stored in the housing 10 are discharged through the inlet through hole 300 of the opening and closing member 310 and then introduced into the holes 321 of the plate body 320. The introduced liquid nutritional components are charged in the containing chamber 220, and then the liquid nutritional components charged in the containing chamber 220 flow downward along the discharge holes 700 of the needles 70 coupled to the through holes 420, whereby the liquid nutritional components are applied to the skin of the person being treated. At the same time, the needles 70 stimulate the skin of the person being treated to stimulate the dermis between the epidermis and the hypodermis of the skin and inject the liquid nutritional components into the dermis, thus activating the skin tissue. This makes it possible to maintain elastic skin and minimize skin aging, thus providing effects such as skin elasticity, aging prevention, and the like through skin nourishment.

When a pressing force acting on the pressing bar 520 is removed, the opening and closing member 310 closes the housing 10. Therefore, as shown in FIG. 7, the liquid nutritional components in the housing 10 are not discharged.

Through the above-described operation, the present invention can easily apply, to the skin, the liquid nutritional components that provide various nutrients to the skin for skin moisturization, anti-inflammation, skin irritation alleviation, whitening, and anti-wrinkle effects, while minimizing damage to the epidermis. In addition, the present invention can stimulate the dermis between the epidermis and the hypodermis of the skin, thus activating skin tissue to maintain elastic skin and minimize skin aging. In particular, the present invention can be conveniently mounted to a glass bottle for easy portability and can inject the liquid nutritional components, which provide various nutrients to the skin for skin moisturization, anti-inflammation, skin irritation alleviation, whitening, and anti-wrinkle effects, into the skin through the needles by using a pumping function. Therefore, the present invention can be convenient, simple, and economically efficient while being used regardless of place.

Embodiment 2

The configuration of this embodiment will be described in detail with reference to FIGS. 8 to 13 as follows.

A housing 10 of this embodiment is similar to the one in Embodiment 1. That is, the housing is a glass bottle type in which liquid nutritional components that provide various nutrients to the skin for skin moisturization, anti-inflammation, skin irritation alleviation, whitening, and anti-wrinkle effects are charged.

Reference numeral 80 denotes a main body. The main body 80 is comprised of a fastening cylinder 810, an inner cylinder 840, an opening and closing plate body 830, a lifting spring 820, and a sliding cylinder 800.

In detail, as shown in FIG. 10, the fastening cylinder 810 is provided at a first end of the main body 80 so as to be mounted on the outer periphery of an upper end opening of the housing 10. The fastening cylinder has an inlet hole 811 formed in the center thereof. The inner cylinder 840 having a hollow cylindrical shape is provided in the fastening cylinder 810 such that a first end thereof is seated on the inner surface of the fastening cylinder. The sliding cylinder 800 is provided at a second end of the inner cylinder 840. The sliding cylinder has a fastening protrusion 801 centrally provided at a surface thereof and multiple needle insertion holes 802 circumferentially formed around the outer periphery of the fastening protrusion 801. The opening and closing plate body 830 is coupled to the fastening protrusion 801. The opening and closing plate body has a first side portion provided with an insertion hole 831 centrally formed therein and has a funnel shaped second side portion. The lifting spring 820 is provided between the sliding cylinder 800 and the fastening cylinder 810.

Meanwhile, a top casing 60 is similar to the one in Embodiment 1. As shown in FIG. 9, the top casing is provided at a second end of the main body 80 and has needle holes 600 communicating with the needle insertion holes 802.

Next, a needle 70 is similar to the one in Embodiment 1. The needle 70 is coupled in the main body 80 and sequentially passes through each of the needle insertion holes 802 and each of the needle holes 600. The needle has a discharge hole 700 centrally formed therein.

The operation of Embodiment 2 configured as described above will now be described.

The operation is shown in FIGS. 11 to 13. First, FIG. 12 shows a coupling state of Embodiment 2.

In the housing 10, the liquid nutritional components that provide various nutrients to the skin for skin moisturization, anti-inflammation, skin irritation alleviation, whitening, and anti-wrinkle effects are charged. In this state, when an operator turns the housing 10 while holding the housing upside down as shown in FIG. 12, the nutritional components are discharged and charged in the inlet hole 811 of the fastening cylinder 810 and further in the inner cylinder 840, in the sliding cylinder 800. The nutritional components are also charged in the discharge holes 700 of the needles 70 to some extent.

When the housing 10 is pressed in such a state, the lifting spring 820 coupled between the fastening cylinder 810 and the sliding cylinder 800 is compressed, causing the sliding cylinder 800 and the top casing 60 to be moved upward. This causes the funnel shaped second side portion of the opening and closing plate body 830 to be expanded to a certain shape, thus closing the inlet hole 811, whereby the charged nutritional components are discharged through the discharge holes 700 of the needles 70.

As a result, the liquid nutritional components are applied to the skin of the person being treated. At the same time, the needles 70 stimulate the skin of the person being treated to stimulate the dermis between the epidermis and the hypodermis of the skin and inject the liquid nutritional components into the dermis, thus activating the skin tissue. This makes it possible to maintain elastic skin and minimize skin aging, thus providing effects such as skin elasticity, aging prevention, and the like through skin nourishment.

When a pressing force acting on the housing 10 downward is removed, as shown in FIG. 12, the liquid nutritional components are not discharged through the discharge holes 700.

Through the above-described operation, the present invention can easily apply, to the skin, the liquid nutritional components that provide various nutrients to the skin for skin moisturization, anti-inflammation, skin irritation alleviation, whitening, and anti-wrinkle effects, while minimizing damage to the epidermis. In addition, the present invention can stimulate the dermis between the epidermis and the hypodermis of the skin, thus activating skin tissue to maintain elastic skin and minimize skin aging. In particular, the present invention can be conveniently mounted to a glass bottle for easy portability and can inject the liquid nutritional components, which provide various nutrients to the skin for skin moisturization, anti-inflammation, skin irritation alleviation, whitening, and anti-wrinkle effects, into the skin through the needles by using a pumping function. Therefore, the present invention can be convenient, simple, and economically efficient while being used regardless of place.

Although the exemplary embodiments of the present invention have been described for illustrative purposes, those skilled in the art will appreciate that various modifications, additions and substitutions are possible, without departing from the scope and spirit of the invention as disclosed in the accompanying claims.

Therefore, the scope of the invention should be determined on the basis of the descriptions in the appended claims, not any specific embodiment, and all equivalents thereof should belong to the scope of the invention.

The present invention can be used to more easily percutaneously inject into the body liquid nutritional components having skin moisturization, anti-inflammation, skin irritation alleviation, whitening, and anti-wrinkle effects; and a therapeutic agent or an immune activation agent, such as a vaccine, or a skin elasticity nutritional component for skin care.

The invention claimed is:
1. A manual injector for skin, the injector comprising:
a housing (10) in which liquid nutritional components that provide various nutrients to the skin for skin moisturization, anti-inflammation, skin irritation alleviation, whitening, and anti-wrinkle effects are charged;
a coupling casing (20) mounted on an outer periphery of an upper end opening of the housing (10) and having an inlet hole (200) formed in a center of the coupling casing, a coupling bracket (210) integrally provided with an upper outer periphery of the inlet hole (200), and a containing chamber (220) defined outside an outer periphery of the coupling bracket (210) and in which the liquid nutritional components of the housing (10) that provide various nutrients to the skin for skin moisturization, anti-inflammation, skin irritation alleviation, whitening, and anti-wrinkle effects are introduced and stored;

an opening and closing valve (30) coupled to the inlet hole (200) by passing therethrough so as to be movable upward and downward;

a bottom casing (40) having a slide hole (410) centrally provided in a first surface thereof at a position corresponding to an end of the opening and closing valve (30), peripheral through holes (420) formed outside the slide hole (410) in all directions at predetermined intervals, and a central through hole (430) centrally provided in a second surface thereof in communication with the slide hole (410);

a pumping unit (50) coupled to the bottom casing so as to be slidable upward downward in the slide hole (410), and having a spring (500) that is provided at a side of the pumping unit and has a first end fixed to the coupling bracket (210), a sliding bracket (510) coupled to a second end of the spring (500), and a pressing bar (520) provided in the central through hole (430);

a top casing (60) having needle holes (600) communicating with the peripheral through holes (420) at positions above the central through hole (430) of the bottom casing (40); and needles (70) coupled in the bottom casing and sequentially passing through each of the peripheral through holes (420) and each of the needle holes (600), and having a discharge hole (700) centrally formed therein.

2. The injector of claim 1, wherein the opening and closing valve (30) includes:

an opening and closing member (310) provided at a first side of the valve and coupled to the inlet hole (200) by passing therethrough, the opening and closing member being configured to be movable upward and downward in the inlet hole (200) so as to open and close the upper end opening of the housing (10), and having a smaller diameter than the inlet hole (200) such that an inlet through hole (300) is defined between an outer periphery of the opening and closing member and an inner wall of the inlet hole; and a plate body (320) provided at a second side of the valve and having a larger diameter than the inlet hole (200) so as to be seated over the inlet hole (200), the plate body having multiple holes (321) formed therein such that the liquid nutritional components that provide various nutrients to the skin for skin moisturization, anti-inflammation, skin irritation alleviation, whitening, and anti-wrinkle effects are introduced therethrough.

3. A manual injector for skin, the injector comprising:

a housing (10) in which liquid nutritional components that provide various nutrients to the skin for skin moisturization, anti-inflammation, skin irritation alleviation, whitening, and anti-wrinkle effects are charged;

a main body (80) including a fastening cylinder (810) provided at a first end of the main body so as to be mounted on an outer periphery of an upper end opening of the housing (10) and having an inlet hole (811) formed in a center of the fastening cylinder, an inner cylinder (840) having a hollow cylindrical shape and provided in the fastening cylinder (810) such that a first end thereof is seated on an inner surface of the fastening cylinder, a sliding cylinder (800) provided at a second end of the inner cylinder (840) and having a fastening protrusion (801) centrally provided at a surface of the sliding cylinder and multiple needle insertion holes (802) circumferentially formed outside an outer periphery of the fastening protrusion (801), and an opening and closing plate body (830) coupled to the fastening protrusion (801) and having a first side portion provided with an insertion hole (831) centrally formed therein, and having a funnel shaped second side portion;

a top casing (60) provided at a second end of the main body (80) and having needle holes (600) communicating with the needle insertion holes (802); and needles (70) coupled in the main body and sequentially passing through each of the needle insertion holes (802) and each of the needle holes (600), and having a discharge hole (700) centrally formed therein.

* * * * *